United States Patent
Heinz-Helmer et al.

(10) Patent No.: US 7,439,235 B2
(45) Date of Patent: Oct. 21, 2008

(54) METHOD FOR OBTAINING ESTROGENS FROM MARE'S URINE

(75) Inventors: Rasche Heinz-Helmer, Burgdorf (DE); Rupp Olaf, Auhagen (DE)

(73) Assignee: Solvay Pharmaceuticals GmbH, Hannover (DE)

(*) Notice: Subject to any disclaimer, the term of this patent is extended or adjusted under 35 U.S.C. 154(b) by 259 days.

(21) Appl. No.: 10/857,355

(22) Filed: Jun. 1, 2004

(65) Prior Publication Data

US 2005/0014738 A1    Jan. 20, 2005

Related U.S. Application Data

(63) Continuation of application No. PCT/EP02/13343, filed on Nov. 27, 2002.

(30) Foreign Application Priority Data

Dec. 1, 2001  (DE) ............................... 101 59 161

(51) Int. Cl.
*A61K 31/56* (2006.01)
(52) U.S. Cl. .................................... 514/170
(58) Field of Classification Search .................. 514/170
See application file for complete search history.

(56) References Cited

U.S. PATENT DOCUMENTS

| | | | | |
|---|---|---|---|---|
| 3,769,401 A | * | 10/1973 | Thompson | .................. 424/546 |
| 5,723,454 A | | 3/1998 | Ban et al. | |
| 7,081,451 B2 | * | 7/2006 | Ahnsorge et al. | ........... 514/170 |
| 2003/0105344 A1 | * | 6/2003 | Ahnsorge et al. | |

FOREIGN PATENT DOCUMENTS

| | | |
|---|---|---|
| WO | WO-9808525 A1 | 3/1998 |
| WO | WO-9808526 A1 | 3/1998 |

OTHER PUBLICATIONS

H. Bradlow "Extraction of Steroid Conjugates With a Neutral Resin" *Steroids* (1968) pp. 265-272.
International Search Report.

* cited by examiner

*Primary Examiner*—Barbara P Badio
(74) *Attorney, Agent, or Firm*—Crowell & Moring LLP

(57) ABSTRACT

A method for obtaining an extract from a natural mixture of conjugated estrogens from the urine of pregnant mares (PMU) by solid-phase extraction on semipolar adsorption resins in which the resulting extract meets the pharmaceutical specifications for conjugated estrogens and the content of free estrogens is minimized even if old pregnant mares' urine and/or pregnant mares' urine which has been stored or transported at elevated temperatures is used.

22 Claims, No Drawings

METHOD FOR OBTAINING ESTROGENS FROM MARE'S URINE

CROSS REFERENCE TO RELATED APPLICATIONS

This application is a continuation of international patent application No. PCT/EP02/13343, filed Nov. 27, 2002, designating the United States of America, and published in German as WO 03/048183, the entire disclosure of which is incorporated herein by reference. Priority is claimed based on Federal republic of Germany patent application no. DE 101 59 161.6, filed Dec. 1, 2001.

BACKGROUND OF THE INVENTION

The present invention relates to obtaining a natural mixture of conjugated estrogens from the urine of pregnant mares.

Estrogens are used in medicine for hormone replacement therapy. In particular, estrogen mixtures are used for the treatment and prophylaxis of the disorders of the climacteric period which occur in women after natural or artificial menopause. In these case, natural mixtures of conjugated estrogens such as are found in the urine of pregnant mares have proved particularly effective and readily compatible.

The dissolved solids content in the urine of pregnant mares (=pregnant mares' urine, abbreviated hereafter as "PMU") can naturally vary within wide ranges, and may generally lie in a range of 40 to 90 g dry matter per litre. In addition to urea and other usual urine contents, phenolic constituents are contained in the solids content of the PMU in quantities of about 2 to 5% by weight relative to the dry matter. These phenolic constituents include cresols and dihydro-3,4-bis[(3-hydroxyphenyl)methyl]-2(3H)-furanone, known as HPMF. These may be present in free or conjugated form. The PMU contains a natural mixture of estrogens which is largely present in conjugated form, e.g. as sulphuric acid semi-ester sodium salt (abbreviated hereafter as "sulphate salt"). The content of conjugated estrogens (calculated as estrogen sulphate salt) may be between 0.3 and 1% by weight, relative to the dry matter.

A suitable method is already known from WO 98/08526, with which a largely cresol- and HPMF-free mixture which is depleted in phenolic urine contents and contains the natural estrogen content of the PMU practically completely can be obtained in a solid-phase extraction on a semipolar, in particular non-ionic semipolar, polymeric adsorption resin. This extract is suitable as a starting material for the preparation of pharmaceuticals which contain the natural mixture of conjugated estrogens as active substance constituent.

In order to be able to be used as active substance constituent for pharmaceuticals, the natural mixture of conjugated estrogens which is obtained must however meet certain pharmaceutical specifications, e.g. the specification laid down in the USP (United States Pharmacopeia) or European Pharmacopeia. Also, the content of free estrogens relative to the dry matter should not exceed certain limit values. Normally the pharmaceutical specification requirements set are met by the mixtures of conjugated estrogens obtained from PMU in accordance with the method of WO 98/08526.

It has, however, turned out that the required pharmaceutical specifications, for example the above limit value of the maximum tolerable content of free estrogens, can often not be met when an "aged" urine, e.g. a PMU which has been stored or transported for relatively long periods and/or possibly at elevated temperatures, is used to obtain the natural mixture of conjugated estrogens. This ageing of the PMU should probably be ascribed to the fact that depending on the storage and/or transport conditions the content of conjugated estrogens can decrease over time or at elevated temperatures, while the content of undesirable free estrogens increases as a result. The original composition of the natural mixture of estrogens can thus be adversely changed in aged urine compared with fresh urine. For the natural mixture of conjugated estrogens obtained with the method of WO 98/08526, when the composition of an aged starting product is possibly changed there is often the risk that the extract obtained can no longer meet the required pharmaceutical specifications, in particular the maximum tolerable content of free estrogens. What is particularly disadvantageous about this is that batches obtained from aged PMU with the active-substance extract, which is valuable in itself, of the mixture of conjugated estrogens can then no longer be used for the production of a pharmaceutical preparation and therefore have to be discarded. The loss of a valuable natural pharmaceutical active substance, in view of the costly collection of PMU, which can only be carried out during certain periods of pregnancy, and the logistical boundary conditions which this involves in practice and from economic points of view, is highly unsatisfactory.

SUMMARY OF THE INVENTION

It is therefore an object of the present invention to provide an industrially and economically optimum method for obtaining a natural mixture, depleted in phenolic urine contents, of conjugated estrogens from PMU, in which even aged PMU, i.e. PMU which has been stored or transported for relatively long periods and/or at elevated temperatures, which may possibly have an elevated proportion of free estrogens, can be used reliably as starting product without rejects, and in which in particular the natural mixture of conjugated estrogens obtained from this PMU has good active-substance contents and meets the required pharmaceutical specification, in particular also with regard to the maximum tolerable content of free estrogens.

A method has now been discovered with which in surprisingly simple manner a mixture of conjugated estrogens can be obtained even from aged PMU, i.e. in particular from a PMU possibly containing an increased proportion of free estrogens, the mixture of conjugated estrogens obtained having a high product quality and reliably meeting the requirements of pharmaceutical specification, in particular also with regard to the maximum tolerable content of free estrogens.

The method according to the invention departs from the method described in WO 98/08526, which serves for obtaining a natural mixture, depleted in phenolic urine contents, of conjugated estrogens from the PMU. Accordingly, the invention relates to a method for obtaining a natural mixture, depleted in phenolic urine contents, of conjugated estrogens from pregnant mares' urine, in which a) a urine, which optionally represents a urine freed of mucilaginous substances and solids, a reduced concentrate of this urine or a reduced urine retentate obtained by membrane filtration of this urine, is contacted with an amount of a semipolar polymeric adsorption resin sufficient for the adsorption of the mixture of conjugated estrogens contained in the urine and a semipolar polymeric adsorption resin laden with the mixture of conjugated estrogens is separated from the rest of the urine, b) the semipolar polymeric adsorption resin laden with the mixture of conjugated estrogens is washed with a washing water set to a pH range of at least 12.0, in particular of 12.5 to 14.0, c) the washed adsorption resin is contacted with an amount of an elution liquid, sufficient for the desorption of the mixture of conjugated estrogens adsorbed thereon, which represents a water-miscible organic solvent from the group of water-miscible ethers, lower alkanols and lower aliphatic ketones or a mixture of the water-miscible organic solvent and water which has optionally been rendered alkaline, and an eluate containing the natural mixture of conjugated estrogens is separated from the adsorption resin and optionally reduced, the method according to the invention being distinguished with respect to the method of the prior art in that between the process steps b) and c) an intermediate washing operation is carried out, in which the semipolar adsorption resin laden with the mixture of conjugated estrogens is washed with water.

The batch preparation, the known process steps a), b) and c) and also the use of the eluate obtained in process step c), which contains a mixture of natural conjugated estrogens, are already described generally in international patent application WO 98/08526 and are thus familiar to the person skilled in the art from this published patent application. The contents of this WO 98/08526 are also made the subject of the present application for the purposes of the disclosure. Further details on the general procedure and materials which can be used are compiled in the examples section of the present application. For example, in accordance with WO 98/08526 semipolar, in particular non-ionic semipolar, adsorption resins may be used. Furthermore, according to the method of the present invention it is surprisingly also possible to use other adsorption resins together with the intermediate washing operation according to the invention, without the product quality or the pharmaceutical specification to be met being adversely affected. The adsorption resins usable within the scope of the present invention will be explained in greater detail further below in the description.

According to the invention, the semipolar adsorption resin laden with the mixture of conjugated estrogens in process step a) is then washed with water in an intermediate washing operation following process step b). The amount of washing water is selected such that the eluate obtained in the subsequent process step c) has a mixture of conjugated estrogens which meets the requirements of a maximum content of free estrogens and thus can be used as active substance constituent for pharmaceuticals. For example, the use of 2 to 8, preferably 3 to 5, bed volumes washing water per bed volume adsorption resin has proved advantageous. In this case, the washing water is advantageously passed through a reactor containing the adsorption resin at a throughflow rate of 3 to 10, preferably 5 to 7, parts by volume washing water per 1 part by volume adsorption resin per hour.

It is altogether surprising that a supposedly simple washing of the adsorption resin with water performed between process steps b) and c), even when using aged PMU, in this way leads to the optimisation of the pharmaceutical specification of the natural mixtures of conjugated estrogens obtained as active substance-extract, as was established according to the invention. In particular it is very surprising that the elevated proportion of free estrogens possibly contained above all in aged PMU can be reduced reliably such that a mixture of natural conjugated estrogens can be obtained as eluate in process step c) which meets the stringent requirements in terms of pharmaceutical specification, for example the requirements drawn up in accordance with the USP or the European Pharmacopeia, and in particular a high-quality and high-quantity active-substance extract containing natural conjugated estrogen mixtures can be obtained even from aged PMU. These active-substance extracts reliably comply with the maximum tolerable maximum contents of free estrogens independently of the age and origin of the PMU used, and thus prove an advantageous and valuable starting product for the preparation of pharmaceuticals. An undesirable and economically disadvantageous loss of valuable pharmaceutical raw materials, such as, in this case, the mixtures of natural conjugated estrogens, can thus be avoided even under difficult conditions.

It has proved a further advantage in the method according to the invention that the eluate obtained in process step c), compared with the prior art, has, relative to the dry matter, an increased total hormone content. By means of this, a quality product is obtained which is distinctly improved e.g. in relation to the active-substance content.

In one advantageous embodiment of the method according to the invention, the intermediate washing is carried out at temperatures below room temperature, particularly at temperatures between 0° C. and 10° C., since it has been shown that losses of hormone or active substance possibly due to the additional intermediate washing operation can be considerably reduced. Usually the ambient temperature is regarded as "room temperature", e.g. the term designates a temperature of between 20° and 30° C. It is very advantageous to perform the method at temperatures of actually 0° C. or approximately 0° C. In practice, it is therefore recommended to operate at temperatures of close to but above 0° C. and to ensure that the aforementioned temperature ranges are is maintained by suitable measures. Conventional measures for lowering the temperature may be used for this, e.g. the use of cooled reactors, cooled materials and/or cooled starting materials such as PMU. From practical points of view a temperature range from 0° C. to about 5° C., in particular of 0° C. to about 3° C., can be considered as temperatures of 0° C. or of approximately 0° C.

In order to keep any hormone losses during the intermediate washing as low as possible, according to this variant of the invention the washing water used in the intermediate washing operation and/or also the washing water which has been rendered alkaline used in process step b) will be precooled to temperatures below room temperature, in particular to temperatures between 0° C. and 10° C. Further advantageous or preferred temperature ranges are, as stated above, temperatures of 0° C. to about 5° C., in particular of from 0° C. to about 3° C. Preferably operation is at temperatures of 0° C. or of approximately 0° C., i.e. preferably the washing water used in the intermediate washing operation and/or also the washing water which has been rendered alkaline used in process step b) is precooled to temperatures close to but above 0° C. By the use of cooled washing water which has been rendered alkaline in process step b), a type of precooling or maintaining of the cooling of the adsorption resin which has already taken place is achieved, e.g. in order to prevent undesirable reheating of the water from taking place when using cooled washing water for the intermediate washing. Preferably therefore the intermediate washing and the preceding process step b) are both carried out in the temperature range, e.g. at temperatures below room temperature, in particular at temperatures between 0° C. and 10° C., or preferably in the same temperature ranges as stated above.

In the foregoing variant of the invention, in which the method is carried out at temperatures below room temperature, it may be desirable to use all devices used, such as reactors for receiving the semipolar adsorption resin or reactors already containing same and/or the PMU used, precooled accordingly to temperatures below room temperature, in particular to temperatures between 0° C. and 10° C., or to the preferred temperature ranges given above.

Suitable adsorbents for use for the method according to the invention are polymeric adsorption resins. Particularly preferred adsorption resins are semipolar, in particular non-ionic semipolar, polymeric adsorption resins. The semipolar polymeric adsorption resins usable as adsorbent in the method according to the invention are preferably porous organic non-ionic polymers, which in contrast to non-polar hydrophobic polymeric adsorption resins have an intermediate polarity (=e.g. with a dipole moment of the active surface of the resin in the range of 1.0 to 3.0, in particular 1.5 to 2.0, Debye) and a somewhat more hydrophilic structure, for example polycarboxylic acid ester resins. Advantageously, macroporous semipolar resins with preferably macroreticular structure and with average pore diameters in the range of 50 to 150, preferably 70 to 100, Angstrom and a specific surface area in the range of 300 to 900, preferably 400 to 500, $m^2/g$ are used. Macroporous cross-linked aliphatic polycarboxylic acid ester resins, in particular cross-linked polyacrylate resins such as e.g. Amberlite XAD-7$^R$ from Rohm und Haas, which represent non-ionic semipolar adsorption resins, have proved particularly suitable.

In addition to the adsorbents named as preferable, other adsorption resins may also be used. Non-polar, semipolar and also polar adsorption resins are all suitable as adsorption resins. The amount of urine which can be pumped through the adsorber should in this case be determined beforehand by means of the respective adsorber capacity. Examples of adsorption resins which can be used are commercially available types such as polymeric Amberlite adsorbents with styrene divinylbenzene parent structures (e.g. types XAD-1180, XAD-2, XAD-4, XAD-16), with acrylic ester parent structures (e.g. XAD-7) or those with highly polar parent structures containing nitrogen and oxygen (e.g. XAD-12). Other adsorption resins are Dowex resins (copolymers of styrene and divinylbenzene), such as Dowex 112, Dowex Optipore, Dowex Optipore V 493; Lewatits (cross-linked polystyrenes), e.g. Lewatit OC 1064, Lewatit OC 1066 or Lewatit OC 1163, polyamine anion-exchanger resins, e.g. Dowex resins. Advantageous adsorption resins are in particular XAD-7, XAD-16 (Type HP), XAD 118 and Dowex Optipore, preferably as Dowex Optipore V 493, and Lewatits OC 1064, OC 1066 and OC 1163.

The method according to the invention, as already described above in detail, has a number of advantages and improvements compared with the prior art. Thus the invention permits the use even of aged PMU, which may also have an elevated proportion of free estrogens, without jeopardising pharmaceutical specifications which have to be met. The method according to the invention therefore also has economic advantages, since the risk [words missing] valuable active substances if the pharmaceutical specification is not met, e.g. in the case of contents of free estrogens which are no longer tolerable, is considerably reduced. The method according to the invention provides an improved-quality active substance constituent with increased hormone content relative to the dry-matter content. This active substance constituent is excellently suitable for the preparation of pharmaceuticals which contain a mixture of natural conjugated estrogens as active substance.

The following examples are intended to explain the invention in further detail without limiting its scope.

EXAMPLES

In the following examples there are given general operating procedures for obtaining active-substance extracts from PMU which contain the natural mixture of the conjugated estrogens contained in the PMU and are largely depleted in phenolic urine contents. It is demonstrated how a quality extract with high active-substance contents can be obtained according to the invention even from aged PMU, which may have an elevated proportion of free estrogens.

Method of WO 98/08526

For the method according to the invention, just as in accordance with WO 98/08526, the PMU as such, a concentrate obtained therefrom by reduction or a retentate obtained therefrom by membrane filtration can be used. The collected urine is first freed in known manner from mucilaginous substances and solids. Solids and mucilaginous substances are desirably allowed to settle and are then separated using known separation methods, for example decanting, separation and/or filtering. Thus the PMU may be passed for example through a known separating means, e.g. a separator, a filtration unit or a sedimenter. A sand bed for example may serve as separating means, or commercially available separators may be used, e.g. nozzle or chamber separators. If desired, a microfiltration unit or an ultrafiltration unit may also be used, and if these are used it is possible to achieve a largely bacteria-free and virus-free filtered PMU at the same time.

If desired, preservatives, germicides, bactericides and/or anthelmintics may be added to the urine.

If a concentrated PMU retentate is to be used instead of the PMU, this can be obtained from the PMU by known membrane filtration. The solids content of the retentate and the composition thereof may vary depending on the PMU used and the membrane used for the membrane filtration, for example the pore width thereof, and also the conditions of filtration. For example, when using a nanofiltration membrane virtually loss-free concentration of the estrogen content in the PMU retentate can be achieved while simultaneously removing up to 50% by weight of the low-molecular PMU contents. PMU retentates which have been concentrated up to a ratio of approximately 1:10, for example a ratio of approximately 1:7, and the volume of which can thus be reduced to approximately 1/10, for example approximately 1/7, of the original PMU volume can be used for the method according to the invention.

The semipolar polymeric adsorption resins usable in process step a) are porous organic non-ionic polymers, which in contrast to non-polar hydrophobic polymeric adsorption resins have an intermediate polarity (=e.g. with a dipole moment of the active surface of the resin in the range of 1.0 to 3.0, in particular 1.5 to 2.0, Debye) and a somewhat more hydrophilic structure, for example polycarboxylic acid ester resins. Advantageously, macroporous semipolar resins with preferably macroreticular structure and with average pore diameters in the range of 50 to 150, preferably 70 to 100, Angstrom and a specific surface area in the range of 300 to 900, preferably 400 to 500, $m^2/g$ are used. Macroporous cross-linked aliphatic polycarboxylic acid ester resins, in particular cross-linked polyacrylate resins such as e.g. Amberlite XAD-7$^R$ from Rohm und Haas, have proved particularly suitable.

The adsorption of the conjugated estrogens on the semipolar adsorption resin can be effected in accordance with WO 98/08526 and also in the present method according to the invention by contacting the PMU or the retentate thereof with the adsorption resin, by introducing the urine into a reactor containing the adsorption resin and keeping it in contact with the adsorption resin therein for a sufficient time for adsorption of the estrogen content. Once adsorption of the conjugated estrogens on the semipolar adsorption resin has taken place, the adsorption resin laden with the mixture of conjugated estrogens can be separated from the rest of the urine in known manner. Advantageously, the urine can be passed through a column containing the adsorption resin at such a throughflow rate that the contact time is sufficient for adsorption of the estrogen content. Suitable examples are throughflow rates which correspond to a throughflow of 3 to 10, preferably 5 to 7, parts by volume PMU/1 part by volume adsorption resin/hour. Advantageously, the throughflow rate of the urine through the reactor can be controlled by operating at a slight excess pressure or partial vacuum. The amount of semipolar adsorption resin to be used may vary according to the type of adsorption resin used and the amount of the solids content in the urine. When using PMU/1 for example one part by volume adsorption resin, e.g. cross-linked aliphatic polycarboxylic acid ester adsorption resin, may be laden with up to 80 parts by volume pretreated PMU, without perceptible amounts of estrogen being detectable in the urine flowing out. When using a PMU concentrate or PMU retentate, the loading capacity of the adsorption resin is of course reduced to the extent by which they are concentrated. Thus for example 1 part by volume of cross-linked aliphatic polycarboxylic acid ester adsorption resin may be laden with an amount of urine corresponding to 20 to 80, preferably 30 to 50, parts by volume PMU.

The semipolar adsorption resin laden with the mixture of conjugated estrogens is washed in process step b) with a washing water set to a pH range of at least 12.0, in particular of 12.5 to 14, preferably approximately 12.5 to 13.5. Washing waters which can be used are aqueous solutions of inert basic substances soluble in the urine, which are strong enough to achieve a pH value of at least 12.5. Suitable water-soluble basic substances which are inert with respect to the semipolar polymeric adsorption resin are preferably water-soluble inorganic bases such as alkali metal or alkaline-earth metal hydroxides, in particular sodium hydroxide. Advantageously the washing water contains only about the amount of basic substances which is required to achieve the desired pH value, preferably approximately pH 13. The amount of washing water is selected such that it is sufficient largely to remove phenolic urine contents without significant amounts of conjugated estrogens being washed out with them. For example, the use of 2 to 10, in particular 4 to 6, bed volumes washing liquid per bed volume adsorption resin has proved advantageous. In this case, the washing water is advantageously passed through a cartridge containing the adsorption resin at a throughflow rate of 3 to 10, preferably 5 to 7, parts by volume washing water/1 part by volume adsorbent/hour.

In process step c), the washed adsorption resin laden with the mixture of conjugated estrogens is then treated with an amount of an elution liquid sufficient for elution of the mixture of conjugated estrogens and an eluate containing the natural mixture of the conjugated estrogens of the PMU is obtained. The elution liquid used according to the invention represents a water-miscible organic solvent from the group of water-miscible ethers, lower alkanols and lower aliphatic ketones or a mixture of such a water-miscible solvent and water which has optionally been rendered alkaline. Suitable ether constituents of the elution liquid are water-miscible cyclic ethers such as tetrahydrofuran or dioxane, but also water-miscible open-chain ethers such as ethylene glycol dimethyl ether (=monoglyme), diethylene glycol dimethyl ether (=diglyme) or ethyloxyethyloxy ethanol (=Carbitol). Suitable lower alkanols are water-miscible alkyl alcohols with 1 to 4, preferably 1 to 3, carbon atoms, in particular ethanol or isopropanol. Suitable lower aliphatic ketones are water-miscible ketones with 3 to 5 carbon atoms, in particular acetone. Elution liquids in which the organic solvent is ethanol have proved particularly beneficial. Advantageously, mixtures of one of the afore-mentioned water-miscible organic solvents and water which has optionally been rendered alkaline are used as elution liquids. The pH value of such water-containing eluents lies in the neutral to alkaline range up to pH 13 and may advantageously be approximately 10 to 12. A solvent which is stable in the pH range used is selected as the solvent component in the water-containing elution liquid. In water-containing alkaline elution liquids having pH values of approximately 10 to 12, lower alkanols, preferably ethanol, are suitable as solvent components. The desired pH value of the water-containing eluent is set by adding a corresponding amount of a water-soluble inert basic substance, preferably an inorganic base, for instance an alkali metal or alkaline earth metal hydroxide, in particular sodium hydroxide. In water-containing elution liquids there may be a volume ratio of water-miscible organic solvent to water in the range of 40:60 to 20:80, preferably approximately 30:70. The amount of eluent used may be approximately 3 to 10, in particular approximately 4 to 6, bed volumes per bed volume adsorption resin. Advantageously, the elution liquid is passed through a reactor containing the adsorption resin laden with the estrogen mixture at such a throughflow rate that the contact time is sufficient for complete elution of the mixture of conjugated estrogens. When using a mixture of ethanol with water in a volume ratio of 30:70, for instance throughflow rates of 3 to 10, preferably 5 to 7, parts by volume elution liquid per 1 part per volume adsorption resin per hour are suitable. Advantageously, the elution is performed in a temperature range from room temperature to approximately 60° C., preferably at approximately 40 to 50° C. If desired, the throughflow rate is regulated by operating at slightly elevated pressure, e.g. at an excess pressure of up to 0.2 bar, and the eluate is collected in several fractions. The contents of conjugated estrogens and phenolic urine contents such as cresols and HPMF in the individual eluate fractions may be determined in known manner by high-performance liquid chromatography (abbreviated "HPLC").

Upon elution, initially a slightly-colored to colorless, practically estrogen-free preliminary fraction is obtained, the amount of which corresponds generally to approximately one bed volume. The bulk of the conjugated estrogens, for instance between 80 and 99% of the conjugated estrogens present in the starting PMU, is in the subsequent dark-yellow-brown colored main eluate fractions, the amount of which is generally 2 to 4 bed volumes. Generally only traces of conjugated estrogens are contained in the subsequent last fractions. If succeeding fractions are obtained which still have a content of conjugated estrogens of above 10% by weight relative to dry matter and less than 0.6% by weight relative to dry matter of cresols and HPMF, these may be combined with the estrogen-rich main eluate for further processing.

Example 1

Comparison Example a) Adsorption of the Estrogen Content of the PMU on a Semipolar Polyacrylate Adsorption Resin A column of a height of 220 mm and a diameter of 40 mm was filled with 300 ml of a semipolar polyacrylate adsorption resin (=Amberlite XAD-7, manufactured by Rohm und Haas, grain size 0.3 to 1.2 mm, dipole moment 1.8 Debye, average pore diameter 80 Angstrom, specific surface area approximately 450 $m^2/g$ dry) swollen in water. 10.5 l (=35 bed volumes) of a PMU (for contents of oestrone sulphate salt and cresol determined by means of HPLC see following table of examples) filtered through an ultrafiltration unit was passed through the column at room temperature at a throughflow rate on average of 24 ml/min (=4.8 bed volumes per hour). The estrogen content of the PMU was fully adsorbed on the semipolar adsorption resin column thus laden. The urine running off was investigated for its content of conjugated estrogens (calculated as oestrone sulphate salt) by means of HPLC and proved to be practically estrogen-free. The bottom product was discarded.

b) Washing of the Laden Adsorption Resin Column

The laden adsorption resin column was washed with 1.5 l of an aqueous sodium hydroxide solution with a pH value of 13. To this end, the alkaline washing water was passed through the column at a throughflow rate of on average 24.6 ml/min (=4.9 bed volumes per hour). The washing liquid running off was investigated in terms of its content of oestrone sulphate salt and cresol by means of HPLC. The investigation showed that during the washing phase less than 5% of the total estrogens charged on to the column was washed out.

c) Desorption of the Conjugated Estrogens from the Washed Adsorption Resin Column 1.5 liters of the elution liquid (ethanol/water 30:70) was passed through the column, which had been preheated to the elution temperature given in the table of examples, at a flow rate of 25 ml/min (=5.0 bed volumes per hour). The eluate running off was collected in 5 fractions. The fractions were each 300 ml (=1 bed volume) and were investigated in terms of their content of oestrone sulphate salt and cresol by means of HPLC.

The first fraction contained only traces of estrogen sulphate salt. The eluate appeared colorless to slightly yellowish in color. Then approx. 80 to 98% of the total amount of conjugated estrogens adsorbed on the column is contained in the following fractions 2 to 4. The eluates here had an intensive dark-brown coloring. The last fraction contained only a small amount of estrogen sulphate salt, which can also clearly be seen in the decrease in color intensity. The DM content in % by weight and the contents of oestrone sulphate salt and cresol determined by HPLC in each case are given in the following table of examples for the fractions containing the bulk of the conjugated estrogens. These fractions represent extracts suitable for further galenic processing.

d) Regeneration of the Adsorption Resin Column

For regeneration, the column was first washed with 600 ml of an ethanol/water mixture containing 50% ethanol and having a pH of 12, then with 600 ml of an ethanol/water mixture containing 70% ethanol and having a pH of 12, then with 600 ml 10%-strength aqueous sodium citrate solution and finally with 600 ml distilled water. The entire regeneration took place at a temperature of 45° C. The column can be laden and regenerated many times, for instance up to 40 times.

Example 2

Method According to the Invention

Example 1 was repeated with the intermediate washing operation according to the invention between the process steps b) and c).

Intermediate Washing

The laden adsorption resin column was washed with 900 ml water. To this end, the neutral washing water was passed through the column at an average throughflow rate of 25.0 ml/min (=5.0 bed volumes per hour). The washing liquid running off was investigated in terms of its content of oestrone sulphate salt and cresol by means of HPLC. The investigation showed that during this washing phase only a small portion (at most only about a few percent) of the total estrogens charged on to the column was washed out. According to the invention, however, on performing the method according to the invention the proportion of free estrogens was also reduced (see Example 4).

TABLE I

Results of the comparison example 1 and Example 2 according to the invention

| | Example No. | |
|---|---|---|
| | 1 | 2 |
| Process step a): Starting PMU | | |
| Oestrone mg/l | 86.4 | 92.3 |
| Equilin mg/l | 57.0 | 57.0 |
| Cresol mg/l | 1191.1 | 877.6 |
| Process step b): | | |
| Washing water = aqueous NaOH solution | pH 13 | pH 13 |
| Intermediate washing: | | |
| Washing water = water Washing fraction 1: | Comparison: Intermediate | |
| Oestrone mg/l | washing | 0.0 |
| Equilin mg/l | not | 20.9 |
| Cresol mg/l | performed | 18.0 |
| Washing fraction 2: | | |
| Oestrone mg/l | | 125.0 |
| Equilin mg/l | | 0.0 |
| Cresol mg/l | | 0.0 |
| Washing fraction 3: | | |
| Oestrone mg/l | | 290.6 |
| Equilin mg/l | | 138.0 |
| Cresol mg/l | | 31.5 |
| Process step c): | | |
| Elution liquid | Ethanol/water 30:70 | Ethanol/water 30:70 |
| Elution temperature | 45° C. | 45° C. |
| Eluate fraction 1: | | |
| % by weight DM | 4.3 | 0.2 |
| Oestrone mg/l (% by weight DM) | 0.0 (0.00) | 342.7 (17.14) |
| Equilin mg/l (% by weight DM) | 24.8 (0.06) | 182.6 (9.13) |
| Eluate fraction 2: | | |
| % by weight DM | 1.9 | 0.9 |
| Oestrone mg/l (% by weight DM) | 2788.6 (14.68) | 2053.5 (22.81) |
| Equilin mg/l (% by weight DM) | 1528.0 (8.04) | 1120.1 (12.45) |
| Eluate fraction 3: | | |
| % by weight DM | 0.2 | 0.2 |
| Oestrone mg/l (% by weight DM) | 193.2 (9.66) | 38.9 (1.95) |
| Equilin mg/l (% by weight DM) | 99.8 (4.99) | 19.8 (0.99) |
| Eluate fraction 4: | | |
| % by weight DM | 0.1 | 0.1 |
| Oestrone mg/l (% by weight DM) | 7.1 (0.71) | 0.0 (0.00) |
| Equilin mg/l (% by weight DM) | 9.3 (0.93) | 0.0 (0.00) |

Example 3

Method According to the Invention with Cooling

Reduction in the Hormone Losses During Neutral Washing

The procedures of Examples 1 and 2 were followed except with cooling. The cooling serves to minimize hormone losses during the intermediate washing. If the intermediate washing is carried out with ice water instead of at room temperature, the hormone losses can be reduced by up to approximately 50%, in particular if the temperature is actually 0° C. or approximately 0° C. in the method. In this case, it is recommended not only to charge ice water which, owing to the column contents which are at room temperature, can warm up relatively quickly, but rather the entire column should be cooled to 0° C.

Performance of the Tests

The column temperature of 0° C. necessary for the intermediate washing was achieved by cooling during the preceding basic washing, i.e. the basic washing already took place at 0° C. Charging 5 bed volumes at 0° C. during the basic washing was sufficient to cool the column contents from room temperature to 0° C. The subsequent intermediate washing could then take place at 0° C. In addition to minimizing the hormone losses, the possible influence of temperature on the cresol separation during the basic washing was also investigated.

Two tests were carried out for direct comparison:

Example 3a

Basic washing and intermediate washing at room temperature.

Example 3b

Basic washing and intermediate washing at 0° C.

All the other steps were carried out in a standard procedure such as given above for the method described in WO 98/08526 or in Examples 1 and 2.

Test Results

Table III shows the test parameters and test results at room temperature and with temperature controlled to 0° C. The test results clearly show that:

a) the basic washing, i.e. the removal of cresols, is not adversely affected by reducing the temperature to 0° C. The separation of cresol takes place completely. Table III gives an overview, and b) the hormone losses during the intermediate washing are reduced by about 50% by reducing the temperature. Table II gives an overview.

TABLE II

Hormone losses and their minimization by intermediate washing at 0° C.

| | Example No. | |
|---|---|---|
| | 3a<br>Room temperature<br>(T = approx. 25° C.) | 3b<br>Ice water<br>(T = approx. 0° C.) |
| Oestrone | 2.7% by weight | 1.8% by weight |
| Equilin | 3.4% by weight | 1.4% by weight |

The charging of sodium hydroxide solution at a controlled temperature of 0° C. during the basic washing operation thus offers a simple possibility, without adversely affecting the cresol separation, of likewise reducing the hormone losses of the intermediate washing operation by operating at about 0° C. Lowering the temperature to approximately 0° C. during the intermediate washing makes it possible to minimize, i.e. reduce, the hormone losses which are unavoidable due to the additional intermediate washing by up to about 50%.

The temperature control of the column during the intermediate washing can be achieved in simple manner if the basic washing carried out before the intermediate washing likewise takes place at approximately 0° C. The cresol separation which takes place during the basic washing is not adversely affected by the reduction in temperature.

TABLE III

Performance of the method according to the invention at room temperature and with cooling

| | Example No. | |
|---|---|---|
| | 3a<br>Room temperature<br>(T = approx. 25° C.) | 3b<br>Ice water<br>(T = approx. 0° C.) |
| Process step a):<br>Starting PMU | | |
| Oestrone mg/l | 64.9 | 65.4 |
| Equilin mg/l | 57.9 | 57.6 |
| Cresol mg/l | 329.0 | 333.0 |
| Process step b): | | |
| Washing water = aqueous NaOH solution | pH 13 | pH 13 |
| Washing fraction 1: | | |
| Oestrone mg/l | 4.4 | 1.7 |
| Equilin mg/l | 0.0 | 1.6 |
| Cresol mg/l | 55.1 | 51.6 |
| Washing fraction 2: | | |
| Oestrone mg/l | 28.8 | 27.9 |
| Equilin mg/l | 31.5 | 24.8 |
| Cresol mg/l | 6942.5 | 7011.0 |
| Washing fraction 3: | | |
| Oestrone mg/l | 0.0 | 0.0 |
| Equilin mg/l | 11.5 | 18.3 |
| Cresol mg/l | 2215.2 | 2774.0 |
| Washing fraction 4: | | |
| Oestrone mg/l | 0.0 | 0.6 |
| Equilin mg/l | 0.0 | 3.2 |
| Cresol mg/l | 280.6 | 268.6 |
| Washing fraction 5: | | |
| Oestrone mg/l | 0.0 | 0.0 |
| Equilin mg/l | 0.0 | 0.0 |
| Cresol mg/l | 76.6 | 44.1 |
| Hormone losses washing fraction 1-5 | | |
| Oestrone | 1.5% | 1.3% |
| Equilin | 2.1% | 2.4% |
| Intermediate washing:<br>Washing water = water<br>Washing fraction 1: | | |
| Oestrone mg/l | 0.0 | 0.0 |
| Equilin mg/l | 0.0 | 0.0 |
| Cresol mg/l | 22.8 | 19.4 |

TABLE III-continued

Performance of the method according to the
invention at room temperature and with cooling

|  | Example No. | |
| --- | --- | --- |
|  | 3a<br>Room<br>temperature<br>(T = approx.<br>25° C.) | 3b<br>Ice<br>water<br>(T = approx.<br>0° C.) |
| Washing fraction 2: | | |
| Oestrone mg/l | 13.3 | 8.2 |
| Equilin mg/l | 9.7 | 5.9 |
| Cresol mg/l | 33.2 | 11.8 |
| Washing fraction 3: | | |
| Oestrone mg/l | 48.0 | 32.0 |
| Equilin mg/l | 58.3 | 23.3 |
| Cresol mg/l | 76.0 | 0.0 |
| Hormone losses washing fraction 1-3 | | |
| Oestrone | 2.7% | 1.8% |
| Equilin | 3.4% | 1.4% |
| Process step c): | | |
| Elution liquid | Ethanol/water<br>30:70 | Ethanol/water<br>30:70 |
| Elution temperature | 45° C. | 45° C. |
| Eluate fraction 1: | | |
| % by weight DM | 0.2 | 0.2 |
| Oestrone mg/l (% by weight DM) | 76.0 (3.80) | 58.0 (2.90) |
| Equilin mg/l (% by weight DM) | 65.8 (3.29) | 48.2 (2.41) |
| Eluate fraction 2: | | |
| % by weight DM | 1.0 | 0.9 |
| Oestrone mg/l (% by weight DM) | 1237.0 (12.37) | 1145.6 (12.73) |
| Equilin mg/l (% by weight DM) | 1093.8 (10.94) | 1135.0 (12.61) |
| Eluate fraction 3: | | |
| % by weight DM | 0.4 | 0.5 |
| Oestrone mg/l (% by weight DM) | 607.8 (15.20) | 840.0 (16.80) |
| Equilin mg/l (% by weight DM) | 524.7 (13.12) | 748.4 (14.97) |
| Eluate fraction 4: | | |
| % by weight DM | 0.1 | 0.1 |
| Oestrone mg/l (% by weight DM) | 84.6 (8.46) | 144.6 (14.46) |
| Equilin mg/l (% by weight DM) | 58.2 (5.82) | 107.4 (10.74) |
| Cresol mg/l (% by weight DM) | 0.0 (0.00) | 0.0 (0.00) |
| Eluate fraction 5: | | |
| % by weight DM | 0.1 | 0.1 |
| Oestrone mg/l (% by weight DM) | 21.1 (2.11) | 34.3 (3.43) |
| Equilin mg/l (% by weight DM) | 7.5 (0.75) | 17.9 (1.79) |
| Eluate fraction 6: | | |
| Oestrone mg/l | 9.0 | 15.2 |
| Equilin mg/l | 0.0 | 3.4 |

Example 4

Reduction of the Content of Free Hormones

In accordance with the procedures of the preceding Examples 1 to 3, it was investigated how the content of free hormones was reduced upon application of the method according to the invention. The results are shown in Table IV a below (comparison tests without intermediate washing) and IV b (tests according to the invention with intermediate washing).

Table IV Minimizing of the free hormones:

TABLE IV a

Comparison tests without intermediate washing

|  | Content of free<br>estrogens in the<br>concentrate<br>(% by weight) | Total content<br>of conjugated estrogens<br>relative to the dry-matter<br>content in the concentrate<br>(% by weight) |
| --- | --- | --- |
| Test 1 | 3.21 | 3.2 |
| Test 2 | 3.67 | 4.4 |
| Test 3 | 2.38 | 9.2 |
| Test 4 | 4.14 | 12.2 |
| Test 5 | 4.03 | 9.9 |

TABLE IV b

Tests with intermediate washing (according to the invention)

|  | Content of free<br>estrogens in the<br>concentrate<br>(% by weight) | Total content<br>of conjugated estrogens<br>relative to the dry-matter<br>content in the concentrate<br>(% by weight) |
| --- | --- | --- |
| Test 6 | 0.0 | 25.2 |
| Test 7 | 0.77 | 17.2 |
| Test 8 | 0.35 | 23.9 |
| Test 9 | 0.20 | 29.3 |
| Test 10 | 0.0 | 27.7 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for obtaining a natural mixture, depleted in phenolic urine contents, of conjugated estrogens from pregnant mares' urine, comprising:
    a) contacting a pregnant mare urine with an amount of a polymeric adsorption resin sufficient to absorb the mixture of conjugated estrogens contained in the urine, and separating a polymeric adsorption resin laden with the mixture of conjugated estrogens from the rest of the urine,
    b) washing the polymeric adsorption resin laden with the mixture of conjugated estrogens with an alkaline washing water which has a pH of at least 12.0, and
    c) contacting the washed adsorption resin with a sufficient amount of an elution liquid to desorb the mixture of conjugated estrogens adsorbed on the resin, said elution liquid comprising a water-miscible organic solvent selected from the group consisting of water-miscible ethers, lower alkanols and lower aliphatic ketones or a mixture of the water-miscible organic solvent and water which has optionally been rendered alkaline, and separating an eluate containing the natural mixture of conjugated estrogens from the adsorption resin, and optionally concentrating the separated eluate,
    wherein the polymeric adsorption resin laden with the mixture of conjugated estrogens is washed with water in an intermediate washing between process steps b) and c).

2. A method according to claim 1, wherein the urine in step a) is a urine freed of mucilaginous substances and solids, a reduced concentrate of such urine or a reduced urine retentate obtained by membrane filtration of such urine.

3. A method according to claim 1, wherein said intermediate washing is carried out at temperatures below room temperature.

4. A method according to claim 3, wherein said intermediate washing is carried out at a temperature between 0° C. and 10° C.

5. A method according to claim 4, wherein said intermediate washing is carried out at a close to but above 0° C.

6. A method according to claim 1, wherein the washing water used for the intermediate washing operation is precooled to temperatures below room temperature.

7. A method according to claim 6, wherein the washing water used for the intermediate washing is precooled to a temperature between 0° C. and 10° C.

8. A method according to claim 7, wherein the washing water used for the intermediate washing is precooled to a temperature close to but above 0° C.

9. A method according to claim 1, wherein the alkaline washing water used in step b) is precooled to a temperature below room temperature.

10. A method according to claim 9, wherein the alkaline washing water used in step b) is precooled to a temperature between 0° C. and 10° C.

11. A method according to claim 10, wherein the alkaline washing water used in step b) is precooled to a temperature close to but above 0° C.

12. A method according to claim 1, wherein step b) and the intermediate washing are both carried out at temperatures below room temperature.

13. A method according to claim 12, wherein step b) and the intermediate washing are both carried out at temperatures between 0° C. and 10° C.

14. A method according to claim 13, wherein step b) and the intermediate washing are both carried out at temperatures close to but above 0° C.

15. A method according to claim 1, wherein the polymeric adsorption resin is contained in a reactor, and the reactor containing the adsorption resin is precooled to a temperature below room temperature.

16. A method according to claim 15, wherein the reactor containing the adsorption resin is precooled to a temperature between 0° C. and 10° C.

17. A method according to claim 16, wherein the reactor containing the adsorption resin is pre-cooled to a temperature close to but above 0° C.

18. A method according to claim 16, wherein the pregnant mare urine is pre-cooled to a temperature below room temperature.

19. A method according to claim 18, wherein the pregnant mare urine is pre-cooled to a temperature between 0° C. and 10° C.

20. A method according to claim 19, wherein the pregnant mare urine is pre-cooled to a temperature close to but above 0° C.

21. A method according to claim 1, wherein the adsorption resin is a semipolar adsorption resin.

22. A method according to claim 21, wherein the adsorption resin is a non-ionic semipolar adsorption resin.

* * * * *

UNITED STATES PATENT AND TRADEMARK OFFICE
CERTIFICATE OF CORRECTION

PATENT NO.         : 7,439,235 B2
APPLICATION NO.    : 10/857355
DATED              : October 21, 2008
INVENTOR(S)        : Heinz-Helmer Rasche and Olaf Rupp It is certified that error appears in the above-identified patent and that said Letters Patent is hereby corrected as shown below:

On the title page in Column 1, item [75] should read:

[75] Inventors: Heinz-Helmer Rasche, Burgdorf (DE); Olaf Rupp, Auhagen (DE);

Signed and Sealed this

Fifteenth Day of September, 2009

David J. Kappos
*Director of the United States Patent and Trademark Office*